United States Patent [19]

Tanaka et al.

[11] Patent Number: 4,923,815
[45] Date of Patent: May 8, 1990

[54] PROCESS FOR HEAT TREATING THROMBIN

[75] Inventors: Kenji Tanaka, Nara; Kenmi Miyano, Osaka; Hideo Nishimaki, Nara; Yoshiro Iga, Osaka, all of Japan

[73] Assignee: Green Cross Corporation, Osaka, Japan

[21] Appl. No.: 173,702

[22] Filed: Mar. 25, 1988

[30] Foreign Application Priority Data

Mar. 27, 1987 [JP] Japan ................................. 62-75562

[51] Int. Cl.$^5$ ............................................. C12N 9/00
[52] U.S. Cl. .................................... 435/183; 435/184; 435/188
[58] Field of Search ..................... 435/183, 184, 188

[56] References Cited

U.S. PATENT DOCUMENTS

| | | | |
|---|---|---|---|
| 1,599,930 | 9/1926 | Takamine | 435/188 |
| 1,855,592 | 4/1932 | Wallerstein | 435/188 |
| 2,495,298 | 1/1950 | Szent-Gyorgyi | 435/188 |
| 2,567,747 | 7/1951 | Wallerstein | 435/188 |
| 3,944,470 | 3/1976 | Diehl | 435/188 |
| 3,950,513 | 4/1976 | Jensen | 435/188 |
| 4,080,262 | 3/1978 | Beancamp | 435/188 |
| 4,297,344 | 10/1981 | Schwinn | 424/101 |
| 4,440,679 | 4/1984 | Fernandes | 260/122 |
| 4,585,754 | 4/1986 | Meisner | 435/188 |
| 4,623,717 | 11/1986 | Fernandes | 530/380 |

OTHER PUBLICATIONS

R. Murray, "Viral Hepatitis", *New York Academy of Medicine*, vol. 31, No. 5, pp. 341-358 (May, 1955).

*Primary Examiner*—Peter D. Rosenberg
*Attorney, Agent, or Firm*—Sughrue, Mion, Zinn, Macpeak & Seas

[57] ABSTRACT

An aqueous solution containing thrombin is heated in the presence of at least one stabilizer selected from various sugars to thereby inactivate viruses possibly contaminating said thrombin. According to this process, the inactivation of the contaminating viruses can be achieved while stably maintaining the thrombin. The stabilizing effect of this process can be further enhanced by using an amino acid as a stabilizer in combination with the sugar.

8 Claims, No Drawings

PROCESS FOR HEAT TREATING THROMBIN

FIELD OF THE INVENTION

The present invention relates to a process for heat treating an aqueous solution containing thrombin to thereby inactivate viruses present in the aqueous solution.

BACKGROUND OF THE INVENTION

In order to inactivate viruses possibly contaminating plasma protein, such as albumin, an aqueous solution of the plasma protein has been heat treated (hereinafter referred to as the "liquid heating process") (Murray et al., The New York Academy of Medicine, 31, (5), 341–358 (1955)). The liquid heating process has been believed to be the most effective method for inactivating viruses. The effect of the process in the inactivation of viruses has been epidemiologically proved. Thus, this process has been commonly employed to date.

Among plasma proteins, however, only a few, including albumin, can withstand the above-mentioned liquid heating process. Those plasma proteins having a high physiological or biological activity are highly sensitive to heat and liable to be thermally denatured by this process. As a result, this process frequently can cause a decrease or loss of the activity of the plasma proteins.

Thrombin, which is a protein present in blood, is frequently accompanied by a risk of contamination with viruses, in particular, hepatitis or AIDS virus. Therefore, blood should be heat treated to thereby inactivate the viruses. However, thrombin per se is inactivated when it is heated in the form of an aqueous solution, i.e., in the above-mentioned liquid heating process.

— SUMMARY OF THE INVENTION

An object of the present invention is to provide a process for heat treating an aqueous solution containing thrombin without inactivating thrombin per se.

It has been found in the present invention that when an aqueous solution containing thrombin is heated in order to inactivate contaminating viruses present in the solution, such as hepatitis or AIDS virus, the heat stability of thrombin can be extremely elevated by adding at least a sugar thereto.

Accordingly, the present invention relates to a process for heat treating thrombin which comprises heating a thrombin-containing aqueous solution in the presence of at least a stabilizer selected from various sugars until the viruses possibly contaminating said thrombin are inactivated.

DETAILED DESCRIPTION OF THE INVENTION

The thrombin preparation to be heated in the process of the present invention is a substance having the biological or physiological activity of thrombin and can be obtained by fractionating plasma protein. For example, a preparation obtained by reacting prothrombin isolated from human or bovine plasma with thromboplastin or snake venom in the present of $Ca^{2+}$ can be employed. A commercially available pharmacopoeial preparation may also be used.

The thrombin to be used in the present invention preferably has a specific activity of about 100 to 1,000 U/mg protein. Thrombin activity is expressed in terms of NIH units, with two units of thrombin representing the amount necessary to coagulate 1 ml of human plasma for 15 seconds. Coagulation is determined using the fibrometer (BBL).

The concentration of the thrombin in the aqueous solution ranges preferably from 500 to 5,000 U/ml, in particular from 1,000 to 3,000 U/ml. The pH value of the thrombin solution preferably ranges from 5 to 8.5, more preferably from 5.6 to 7.6

Suitable examples of the sugar to be used as a stabilizer in the present invention include monosaccharides such as glucose and mannose; disaccharides such as maltose, sucrose and lactose; and sugar alcohols such as sorbitol, mannitol and xylitol. Among these, particularly preferred is sucrose.

The sugar may be added in an amount of from 60 to 100 w/v%, preferably 80 to 100 w/v%, per 500 to 5,000 U/ml of thrombin.

In order to further elevate the stabilizing effect in the present invention, it is preferable to add an amino acid to the thrombin-containing aqueous solution. Examples of the amino acid to be used in the present invention include neutral ones such as glycine, serine and threonine; acidic ones such as aspartic acid and glutamic acid; and basic ones such as arginine and lysine. Among these, arginine is particularly preferred.

The amino acid may be added in a concentration of from 0.05 to 5 M, preferably 1 to 4 M, per 500 to 5,000 U/ml of thrombin.

In addition, other conventionally known additives such as calcium chloride or sodium citrate may be used. Calcium chloride is generally added in a concentration of from 0.001 to 1.5 M and sodium citrate is generally added in a concentration of from 0.01 to 1.0 M.

As to the heat treatment, the thrombin-containing aqueous solution is to be heated at a temperature sufficient for the inactivation of the viruses, e.g., 50 to 70° C., preferably about 60° C., for 10 minutes to 20 hours, preferably 5 to 15 hours.

Examples of the viruses to be inactivated according to the present invention include those possibly contaminating human plasma proteins, in particular, hepatitis virus and AIDS virus.

The aqueous solution of thrombin thus heated may be processed in a conventional manner such as dialysis, sterilizing filtration, inoculation or lyophilization.

According to the present invention, a plasma protein preparation can be efficiently produced on an industrial scale since viruses possibly contaminating a valuable blood preparation containing thrombin can be inactivated without significantly lowering the activity of the thrombin.

The following Test Examples and Examples are provided in order to further illustrate the present invention, but are in no way intended to limit the scope of the present invention.

PREPARATION EXAMPLE 1

Prothrombin was purified from normal human plasma by barium chloride adsorption and DEAE-Sephadex ®column chromatography (Bajaj, S.P. et al., J. Biol. Chem., 248, 7729 (1973)). To the thus-obtained prothrombin solution (containing 2 to 10 units of prothrombin; one units of prothrombin is the amount in terms of protein present in 1 ml of normal human plasma), thromboplastin obtained from human placenta in an amount of from 0.1 to 0.3 parts by volume based on the volume of prothrombin solution, human plasma in an amount of from 0.2 to 0.6 parts by volume based on the volume of prothrombin solution and a calcium chloride solution in a concentration of from 0.01 to 0.1 w/v% were added to thereby convert the prothrombin into thrombin. The resulting crude thrombin showed a thrombin activity of 10 U/mg protein. This crude thrombin was then purified by SP-Sephadex ®column chromatography (Lundblad, R.L., Biochemistry, 10, 2501 (1971)) and subsequently the purified thrombin was concentrated and dialyzed against a 100 mM citrate buffer solution (pH 7.0) containing 7.5 w/v% of D-mannitol. Thus, a 3,500 U/ml thrombin solution having a thrombin activity of 500 U/mg protein was obtained.

EXAMPLE 1

To 5 ml of the thrombin solution obtained as in Preparation Example 1, 8 g of sucrose and 4.2 g of arginine were added to give a final concentration of thrombin, sucrose and arginine of 1,500 U/ml, 80 w/v% and 2 M, respectively. Then, the pH value of the resulting solution was adjusted to 6.2 with sodium hydroxide. The solution thus obtained was heat treated at 60° C. for 10 hours. The thrombin preparation thus heated was evaluated in terms of solubility, thrombin activity, cellulose acetate electrophoresis and gel filtration, compared with an unheated sample. No significant changes were not observed. Thus, the thrombin was stable in the heat treatment of the present invention.

EXAMPLE 2

In addition to the stabilizers used in Example 1, 2.8 mg of calcium chloride was further added to 5 ml of a 3,500 U/ml thrombin solution.

The thus-obtained thrombin solution contained 1,500 U/ml of thrombin, 80 w/v% of sucrose, 2 M of arginine and 3 mM of calcium chloride (pH 6.2).

After heat treating at 60° C. for 10 hours, the characteristics of the thrombin were evaluated as in Example 1 and it was found that the stability of this solution was comparable to that of the one described in Example 1.

TEST EXAMPLE 1

Stabilizing effects of various sugars

Thrombin solutions were prepared so as to contain 2,500 U/ml of the purified thrombin (specific activity of 500 U/mg protein) obtained as in Preparation Example 1, 60 w/v% of each sugar as shown in Table 1 below and to have a pH value of 7.0.

The thus-obtained thrombin solutions were heat treated at 60° C. for 10 hours, and then, the residual activity of the thrombin was measured.

The results are shown in Table 1.

TABLE 1

| Sugar | Residual activity (%) |
| --- | --- |
| None | 0 |
| glucose | 60 |
| sucrose | 63 |
| sorbitol | 62 |

From the results in Table 1, it is clear that the stability of thrombin is extremely improved by adding each sugar compared with the control case.

TEST EXAMPLE 2

Stabilizing effects depending on sugar concentration

Thrombin solutions were prepared so as to contain 3,500 U/ml of the purified thrombin (specific activity: 500 U/mg protein) prepared as in Preparation Example 1, sucrose in the amounts shown in Table 2 and to have a pH value of 7.0.

The thus-obtained thrombin solutions were heat treated as in Test Example 1 and the residual activity of the thrombin was determined in the same manner as in Test Example 1.

The results are shown in Table 2.

TABLE 2

| Concentration of sucrose (w/v %) | Residual activity (%) |
| --- | --- |
| 0 | 0 |
| 60 | 60 |
| 80 | 75 |
| 100 | 74 |

As is apparent from the results shown in Table 2, no significant change in the residual activity of the thrombin is observed in the case that the sucrose concentration is 80 w/v% or more. Therefore, it is found that the sugar concentration of 80 w/v% is enough to elevate stability of thrombin. Since the ratio of sterilizing viruses upon heat treatment is generally reduced as the sugar concentration increases, it is desirable to use sugar in a concentration as low as possible unless thrombin activity is reduced.

TEST EXAMPLE 3

Stabilizing effect of combined use

Thrombin solutions were prepared so as to contain 2,700 U/ml of the purified thrombin (specific activity: 500 U/mg protein) prepared as in Preparation Example 1, 80 w/v% of sucrose and 0.1 M of each amino acid shown in Table 3 and to have a pH value of 7.0.

The thus-obtained thrombin solutions were heat treated as in Test Example 1 and the residual activity of the thrombin was determined in the same manner as in Test Example 1.

The results are shown in Table 3.

TABLE 3

| Stabilizer | | Residual activity (%) |
| --- | --- | --- |
| Amino acid | Sucrose | |
| none | none | 0 |
| arginine | none | 0 |
| none | contain | 61 |
| arginine | contain | 85 |
| glycine | contain | 83 |
| serine | contain | 87 |
| threonine | contain | 87 |
| aspartic acid | contain | 84 |

From the results shown in Table 3, it is clear that the combined use of a sugar and an amino acid further improves the stabilizing effect.

TEST EXAMPLE 4

Stabilizing effect depending on amino acid concentration

Thrombin solutions were prepared so as to contain 1,500 U/ml of the purified thrombin (specific activity: 500 U/mg protein) prepared as in Preparation Example 1, 80 w/v% of sucrose and arginine in the amounts shown in Table 4 and to have a pH value of 7.0.

The thus-obtained thrombin solutions were heat treated as in Test Example 1 and the residual activity of the thrombin was determined in the same manner as in Test Example 1.

The results are shown in Table 4.

TABLE 4

| Concentration of arginine (M) | Residual activity (%) |
|---|---|
| 0 | 75 |
| 0.5 | 85 |
| 1.0 | 88 |
| 2.0 | 95 |
| 3.0 | 98 |
| 3.5 | 98 |

As it can be seen in results in Table 4, the residual activity of the thrombin is not less than 95% when the concentration of arginine is 2.0 M or more. Considering the solubility of arginine, it is found that the optimal concentration of arginine is about 2 M.

TEST EXAMPLE 5

Stabilizing effect depending on pH value

Thrombin solutions were prepared so as to contain 1,500 U/ml of the purified thrombin (specific activity: 500 U/mg protein) prepared as in Preparation Example 1, 80 w/v% of sucrose and 2 M of arginine and to have each pH value as shown in Table 5.

The thus-obtained thrombin solutions were heat treated as in Test Example 1 and the residual activity of the thrombin was determined in the same manner as in Test Example 1.

The results are shown in Table 5.

TABLE 5

| pH value | Residual activity (%) |
|---|---|
| 3 | 0 |
| 4 | 2 |
| 5 | 90 |
| 6 | 95 |
| 7 | 93 |
| 8 | 88 |
| 9 | 70 |
| 10 | 47 |

As it can be seen in results in Table 5, it is found that the desirable pH value of the thrombincontaining preparation is about 6 for the purpose of stabilization of thrombin upon heat treatment. As a result of further studies, it is confirmed that the optimal pH value is 6.2.

TEST EXAMPLE 6

Thrombin solutions were prepared so as to contain 1,500 U/ml of the purified thrombin (specific activity: 500 U/mg protein) prepared as in Preparation Example 1, 80 w/v% of sucrose and 2 M of arginine and to have a pH value of 6.2. To the resulting solution, each virus shown in Table 6 suspended in a 10 mM isotonic phosphate buffer solution containing sodium chloride (pH 7.0) was added.

After heat treating the mixture at 60° C. for each period shown in Table 6, the infectivity of the virus was determined with plaque technique (as described in Proc. Natl. Acad. Sci. USA, 38, 747–752 (1952)).

The results are shown in Table 6.

TABLE 6

| | Viral infectivity* | | | | |
|---|---|---|---|---|---|
| Virus | before heating | 60° C. 1 hr | 60° C. 3 hrs | 60° C. 5 hrs | 60° C. 10 hrs |
| vesicular stomatitis v. | $7 \times 10^5$ | $1 \times 10^5$ | $1 \times 10^3$ | <50 | <50 |
| Sindbis v. | $9 \times 10^5$ | $1 \times 10^5$ | $5 \times 10^3$ | <50 | <50 |
| chikungunya v. | $8 \times 10^5$ | $2 \times 10^2$ | <50 | <50 | <50 |
| echovirus | $10^{6.5}$ | $10^{4.3}$ | $10^{2.8}$ | $<10^{2.5}$ | $<10^{2.5}$ |

*Infectities of viruses other than echovirus is expressed in pfu/ml.
Infectivities of echovirus is expressed in $TCID_{50}$/ml.

From the results shown in Table 6, it is apparent that various viruses are inactivated upon the heat treatment of the present invention. Therefore, it is considered that hepatitis or AIDS virus possibly contaminating plasma protein can be inactivated upon the heat treatment according to the preset invention.

While the invention has been described in detail and with reference to specific embodiments thereof, it will be apparent to one skilled in the art that various changes and modifications can be made therein without departing from the spirit and scope thereof.

What is claimed is:

1. A process for heat treating thrombin which comprises heating an aqueous solution containing thrombin in a concentration from about 500 to 5,000 U/ml at a temperature of from 50 to 70° C. for 10 minutes to 20 hours for inactivation of viruses contained therein, in the presence of a combination stabilizer of at least one sugar selected from the group consisting of monosaccharides, disaccharides and sugar alcohols and at least one amino acid selected from the group consisting of glycine, serine, threonine, aspartic acid, glutamic acid, arginine and lysine until viruses contaminating said thrombin are inactivated.

2. The process as claimed in claim 1, wherein the concentration of thrombin in the aqueous solution ranges from about 1,000 to 3,000 U/ml.

3. The process as claimed in claim 1, wherein said sugar is added in an amount of from about 60 to 100 w/v% per 500 to 5,000 U/ml of thrombin.

4. The process as claimed in claim 3, wherein said sugar is added in an amount of from about 80 to 100 w/v% per 500 to 5,000 U/ml of thrombin.

5. The process as claimed in claim 1, wherein said amino acid is added in a concentration of about 0.05 to 5 M per 500 to 5,000 U/ml of thrombin.

6. The process as claimed in claim 5, wherein said amino acid is added in a concentration of about 1 to 4 M per 500 to 5,000 U/ml of thrombin.

7. The process as claimed in claim 1, wherein the pH value of the aqueous solution ranges from about 5 to 8.5.

8. The process as claimed in claim 7, wherein the pH value of the aqueous solution ranges from about 5.6 to 7.6.

* * * * *